United States Patent
Flescher et al.

(10) Patent No.: US 7,683,211 B2
(45) Date of Patent: *Mar. 23, 2010

(54) JASMONATE DERIVATIVE COMPOUNDS PHARMACEUTICAL COMPOUNDS AND METHODS OF USE THEREOF

(75) Inventors: Eliezer Flescher, Hod Hasharon (IL); Yoel Kashman, Tel Aviv (IL); Dorit Reischer, Ra-anana (IL); Shiri Shimony, Tel Aviv (IL)

(73) Assignee: Ramot at Tel-Aviv University Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/198,559

(22) Filed: Aug. 26, 2008

(65) Prior Publication Data

US 2008/0319066 A1 Dec. 25, 2008

Related U.S. Application Data

(63) Continuation of application No. 10/581,546, filed as application No. PCT/IL2004/001098 on Dec. 1, 2004, now Pat. No. 7,425,651.

(60) Provisional application No. 60/526,081, filed on Dec. 2, 2003.

(51) Int. Cl.
*C07C 61/00* (2006.01)
*C07C 69/74* (2006.01)
*A61K 31/215* (2006.01)

(52) U.S. Cl. ............... 562/503; 560/121; 514/530; 514/573

(58) Field of Classification Search ............... 562/503; 560/121; 514/530, 573
See application file for complete search history.

(56) References Cited

U.S. PATENT DOCUMENTS

| | | | |
|---|---|---|---|
| 5,118,711 A | 6/1992 | Wilson et al. | |
| 5,436,226 A | 7/1995 | Lulai et al. | |
| 6,114,284 A | 9/2000 | Fujisawa et al. | |
| 6,469,061 B1 | 10/2002 | Flescher et al. | |
| 7,425,651 B2 * | 9/2008 | Flescher et al. | 562/503 |
| 2002/0173470 A1 | 11/2002 | Flescher et al. | |

FOREIGN PATENT DOCUMENTS

| | | |
|---|---|---|
| JP | 4-41414 A | 2/1992 |
| JP | 10-29935 A | 2/1998 |
| WO | WO 02/080890 A2 | 10/2002 |

OTHER PUBLICATIONS

Derwent publications Ltd., London, AN 1998-163664, xp002203872.

Basaria et al, "Clinical review 138, anabolic-androgenic steroid therapy in treatment of chronic diseases", Journal of clinical endocrinology and metabolism, 86(11):5108-5117, Nov. 2001.

Dangl et al., "Death don't have no mercy: cell death programs in plant-microbe interactions", The Plant Cell, vol. 8, Oct. 1996, p. 1793-1807.

Dermastia, Marina et al., "the effects of a plant growth regulator, jasmonic acid, on some mammalian fibroblast cell lines" Acta Pharm. (Zagreb) 1992, 42(4), 347-50 XP001085225.

Farmer et al., "Interplant communication: Airborne Methyl Jasmonate Induces Synthesis of Proteinase Inhyibitors Plant Leaves", Proc. Natl. Acad. Sci. USA, vol. 87, Oct.1990, p. 7713-7716.

Fingrut O. et al., "Plant stress hormones suppress the proliferation and induce apoptosis in human cancer cells", Bios. Infor. Service, Philadelphia, PA, US, XP000185234, 2002, 2002-04, Accession No. 200200324956 & Leukemia (Basingstoke), vol. 16, No. 4, Apr. 2002, p. 608-616.

Gorospe et al., "Inhibition of G1 Cyclin-Dependent Kinase Activity . . . ", Molecular and Cellular Biology, Mar. 1996, p. 762-770.

Ishii, Y. et al: "Induction of differentiation of human myeloid leukemia cells by jasmonates, plant hormones", Leukemia, 18(18), 1413-1419, 2004 XP002328125.

Kiyota, Hiromasa et al : "(.+-.)-Methyl 11-fluorojasmonate as a designed antimetabolite of methyl jasmonate: synthesis and plant growth regulatory activity" XP002328126 & Nippon Noyaku Gakkaishi, 26(1), 96-99, 2001.

Lidija Klampfer et al., "Sodium salicylate activates caspases and induces apoptosis of myeloid leukemia cell lines", Blood, vol. 93, No. 7 (Apr. 1, 1999), 1999, p. 2386-2394.

Mittler et al., "Sacrifice in the face of foes: pathogen-induced programmed cell death in plants", Trends in Microbiology, vol. 4, No. 1, Jan. 1996, p. 10-15.

Nakaguchi, Osamu et al : "Hair growth stimulants containing dehydrodihydrojasmonic acid lower alkyl esters", XP002328128.

Okano et al., Chemical Abstracts, vol. 127, #200188v, 1997.

Porter et al., "Emerging roles of caspass-3 in Apoptosis", Cell Death and differentiation, 1999, p. 99-104.

Ryals et at., "Systemic Acquired Resistance", The Plant Cell, vol. 8, Oct. 1996, p. 1809-1819.

Schierle K et al., "Homologues of Dihydro-12-oxo-phytodienoic acid and jasmonic acid by mixed kolbe electrolysis", Tetrahedron Letters, Elsevier Science Publishers, Amsterdam, NL, vol. 37, No. 48, Nov. 25, 1996, p. 8715-8718, XP004068758.

Schwenger et al, "Cell-Type-Specific Activation Of C-Jun N-Terminal Kinase By Salicylates", J. Of Cellular Physiology, 179, 1999, p. 109-114.

(Continued)

*Primary Examiner*—Sikarl A Witherspoon
(74) *Attorney, Agent, or Firm*—Browdy and Neimark, PLLC

(57) ABSTRACT

The present invention provides novel jasmonate derivative compounds, methods for their preparation, pharmaceutical compositions including such compounds, and methods of using these compounds and compositions, especially as chemotherapeutic agents for treatment of cancers, especially mammalian cancers.

25 Claims, 8 Drawing Sheets

OTHER PUBLICATIONS

Schwenger et al., "Sodium salicylate induces apoptosis via p38 mitogen-activated . . . ", Proc. Natl. Acad. Sci USA, 1997, p. 2869-2873.

Seiki et al., Chemical abstracts, vol. 126, #196471h, 1998.

Ward, Kerry et al : "The induction of proteinase inhibitor II by jasmonates" XP002328127, accession No. 1997 & Proceeding of the plant growth regulator society of America, $23^{RD}$, 291-294, 1996.

Willingham, "Cytochemical methods for the detection of apoptosis", The J. Of Histochemistry & Cytochemistry, vol. 47, p. 1101-1109, 1999.

Torii, Kousuke et al., "Evaluation of antiandrogen effect using SC-3 cells", Database accession No. 127:200188 XP002203871 & Nippon Koshohin Kagakkaishi (19970, 21(2), 97-102.

Chinese Office Action (for the National Phase of the PCT Application) issued May 16, 2008.

\* cited by examiner

JASMONATE DERIVATIVE COMPOUNDS PHARMACEUTICAL COMPOUNDS AND METHODS OF USE THEREOF

FIELD OF THE INVENTION

The present invention relates to the field of jasmonate derivative compounds, methods for their preparation, pharmaceutical compositions including such compounds, and methods of using these compounds and compositions, especially as chemotherapeutic agents for treatment of cancers, especially cancers in mammals.

BACKGROUND OF THE INVENTION

Jasmonates are a family of plant stress hormones, derived from linolenic acid by the octadecanoid pathway, and are found in minute quantities in many edible plants. Stress hormones such as the jasmonate family, have evolved in plants, and are released in such times of stress such as extreme UV radiation, osmotic shock, heat shock and pathogen attack to initiate various cascades which end in appropriate responses. Examples of members of the jasmonate family are jasmonic acid, which is crucial to intracellular signaling in response to injury, and methyl jasmonate, which causes induction of a proteinase inhibitor that accumulates at low concentrations in response to wounding or pathogenic attacks. Jasmonates have been patented for a variety of uses in plant growth and crop improvement, but have not been previously known for use in medicine. Use of jasmonates for the treatment of mammalian cancer has been disclosed in U.S. Pat. No. 6,469,061, reference to which is incorporated hereby in its entirety. In U.S. Pat. No. 6,469,061, it was shown that jasmonates were directly cytotoxic for various types of human cancer cells derived from breast, prostate, skin and blood cancers. While jasmonates elicited death in human leukemic Molt-4 cells, they did not damage normal lymphocytes.

Subsequent data collected similarly showed that jasmonates do not damage healthy erythrocytes (see WO 02/080890). In U.S. Pat. No. 6,469,061, one jasmonate compound in particular, methyl jasmonate, was shown to be effective in preventing development of lymphomas in mice. See also Fingrut, O. and E. Flescher. 2002. "Plant stress hormones suppress the proliferation and induce apoptosis in human cancer cells", Leukemia 16: 608-616 (2002).

The pharmacological activity of jasmonate compounds makes them attractive candidates as therapeutic agents for the treatment of cancer. Because only a few jasmonate derivatives have been reported (see, for example, Ishii et al., Leukemia, 1-7 (2004)), a need in the art exists to develop jasmonate derivative compounds that are potent chemotherapeutic drugs, with a high degree of specificity towards malignant cells.

The present invention addresses this need, and provides other advantages as well.

SUMMARY OF THE INVENTION

The present invention is directed to jasmonate derivative compounds, especially those that are halogenated. Such compounds include "methyl jasmonate di-bromide", or "MJDB", and "methyl jasmonate tetra-bromide", or "MJTB." These compounds are significantly more potent than the most effective jasmonate disclosed in U.S. Pat. No. 6,469,061, namely, methyl jasmonate. Jasmonate derivatives such as MJDB and MJTB, as shown below, exert selective cytotoxicity on cancerous lymphocytes drawn from patients, while sparing normal lymphocytes.

The present invention also includes including salts, hydrates, solvates, polymorphs, optical isomers, diastereomers, and any mixtures thereof of the compounds of the present invention, especially of MJDB and MJTB.

The compounds of the present invention have the formula:

Formula I

[chemical structure with ring system bearing substituents $R_2$, $R_5$, $R_6$, $R_7$, $R_3$, $R_4$, and groups A, B, C, D, E and $(CH_2)nCOR_1$ side chain]

wherein:

n is 0.1, or 2;

$R_1$ is OH, $C_1$ to $C_{12}$ alkoxy, $C_1$ to $C_{12}$ substituted alkoxy aryloxy, O-glucosyl or imino;

$R_2$ is OH, $C_1$ to $C_{12}$ alkoxy, $C_1$ to $C_{12}$ substituted alkoxy, O-glucosyl, oxo, alkyl or imino;

$R_3$, $R_4$, $R_5$, $R_6$, $R_7$, A, B, C, D and E are each independently H, halogen, OH, $C_1$ to $C_{12}$ alkoxy, $C_1$ to $C_{12}$ substituted alkoxy, aryloxy, O-glucosyl, $C_1$ to $C_{12}$ alkyl or $C_1$ to $C_{12}$ substituted alkyl;

wherein $R_1$ and $R_2$, or $R_1$ and $R_4$ may form together a lactone which is optionally substituted;

wherein the bonds between $C_3:C_7$, $C_4:C_5$, and $C_9:C_{10}$ may independently be double bonds or single bonds;

provided that at least one of $R_3$, $R_4$, $R_5$, $R_6$, $R_7$, A, B, C, D and E is a halogen; and provided that, if A is the only halogen in the compound, that A is not fluoro;

or a derivative of said formula, wherein the derivative has at least one of the following:

a lower acyl side chain at $C_3$ (free acid or ester or conjugate), a keto or hydroxy (free hydroxy or ester) moiety at the $C_6$ carbon, or an n-pentenyl or n-pentyl side chain at $C_7$;

including salts, hydrates, solvates, polymorphs, optical isomers, enantiomers, diastereomers, and mixtures thereof.

More specifically, the preferred compounds of the present invention (Formula I) are those where the bond between $C_9$ and $C_{10}$ is a single bond. Other preferred compounds are where $R_2$ is oxo. Still other preferred compounds are where at least one of $R_6$ and $R_7$ is bromo, iodo, fluoro or chloro. Even more preferred are compounds where both of $R_6$ and $R_7$ are selected from bromo, iodo, fluoro or chloro. Yet more preferred are compounds where both of $R_6$ and $R_7$ are bromo.

A further preferred aspect of the invention are compounds where A, B $R_6$ and $R_7$ me bromo, iodo, fluoro or chloro. Even more preferred are compounds where A, B, $R_6$ and $R_7$ are each bromo.

Other preferred compounds of the present invention are where $R_1$ is alkoxy. In yet another aspect, $R_3$, $R_4$ and $R_5$ are each H (hydrogen). In still another aspect, C, D and E are each H.

One of the most preferred compounds of the present invention is methyl jasmonate di-bromide (MJDB). According to Formula I, MJDB is where: n is 0; the bonds between $C_3:C_7$, $C_4:C_5$, and $C_9:C_{10}$ are single bonds; $R_1$ is methoxy; $R_2$ is oxo; $R_3$, $R_4$, $R_5$, A, B, C, D and E are each H; and $R_6$ and $R_7$ are each bromo.

Another of the most preferred compounds of the present invention is methyl jasmonate tetra-bromide (MJTB).

According to Formula I, MJTB is where: n is 0; the bonds between $C_3:C_7$, $C_4:C_5$, and $C_9:C_{10}$ are single bonds; $R_1$ is methoxy; $R_2$ is oxo; $R_3$, $R_4$, $R_5$, C, D and E are each H; and A, B, $R_6$ and $R_7$ are each bromo.

In other preferred compounds of the invention n is 0; the bonds between $C_3:C_7$, $C_4:C_5$, and $C_9:C_{10}$ are single bonds; $R_1$ is methoxy; $R_2$ is oxo; $R_3$, $R_4$, $R_5$, A, B, C, D and E are each H; and either:

e) $R_6$ and $R_7$ are each fluoro (designated as compound "MJS99");

b) $R_6$ and $R_7$ are each iodo (designated as compound "MJS85f14");

c) $R_6$ and $R_7$ are each chloro (designated as compound "MJS81f13");

d) one of $R_6$ and $R_7$ is bromo and the other is hydroxy (designated as compound "NJ-63"); or e) one of $R_6$ and $R_7$ is iodo and the other is methoxy (designated as compound "MJS72f5).

The present invention also contemplates pharmaceutical compositions that include a pharmaceutically acceptable carrier and, as an active ingredient, the compounds of the invention, as described above. Preferred compositions have as an active ingredient MJDB or MJTB. Preferably, in the pharmaceutical composition the active ingredient is dissolved in any acceptable lipid carrier. Further, in accordance with a preferred embodiment of the present invention, the composition additionally comprises at least one other chemotherapeutic agent.

The present invention additionally provides a method for reduction of the growth of cancer cells, comprising exposing the cancer cells to a therapeutically effective amount of a compound of the invention, as described herein Furthermore, the present invention provides a method for the treatment of cancer, comprising administering to the subject a pharmaceutical composition containing as an active ingredient a therapeutically effective amount of the compound of the invention, as described herein. According to preferred embodiments the cancers are cancers of a warm-blooded vertebrate, more preferably a mammal, most preferably a human.

The cancers include carcinoma, sarcoma, adenoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell and non-small cell lung carcinoma, bladder carcinoma, epithelial carcinoma, glioma, astrocyoma, medulloblastoma, craniopharyngioma, ependynoma, pinealoma, retinoblastoma, rectal carcinoma, cancer of the thyroid, head and neck cancer, brain cancer, cancer of the peripheral nervous system, cancer of the central nervous system, neuroblastoma, cancer of the endometrium, lymphoproliferative diseases, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, as well as metastases of all the above.

These and further features of the present invention will be better understood in conjunction with the drawings, detailed description, and claims that follow.

BRIEF DESCRIPTION OF THE DRAWINGS

The present invention is herein described, by way of example only, with reference to the accompanying drawings, wherein.

DETAILED DESCRIPTION OF THE INVENTION

Figure 1:
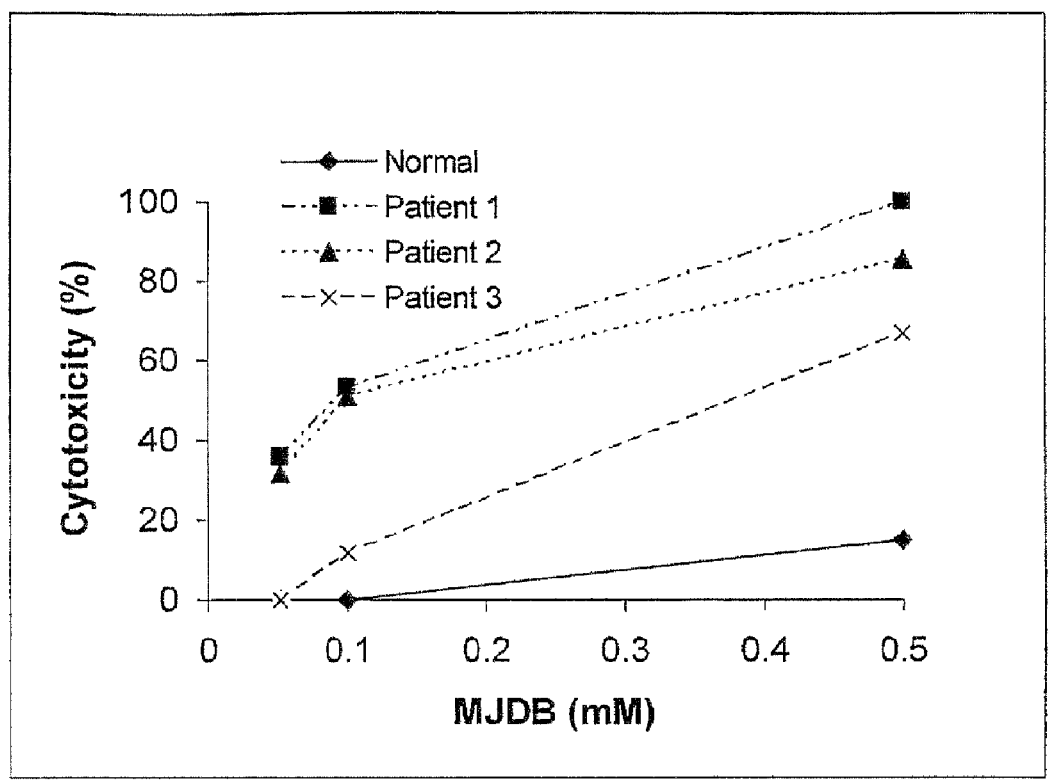
FIG. 1 shows the cytotoxic activity of MJDB against: a) human CLL lymphocytes (labeled "Patient 1," "Patient 2" and "Patient 3"); and b) lymphocytes from healthy donors (labeled "Normal").

The present invention provides novel jasmonate derivatives, compositions comprising these compounds and methods of using the compositions in the treatment of cancer.

The compounds of the present invention have the formula:

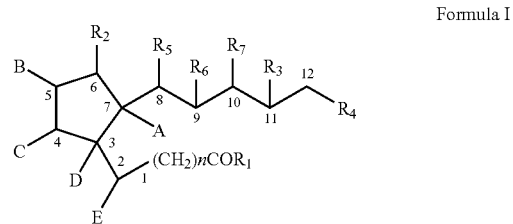

Formula I wherein:

n is 0, 1, or 2;

$R_1$ is OH, $C_1$ to $C_{12}$ alkoxy, $C_1$ to $C_{12}$ substituted alkoxy, aryloxy, O-glucosyl or imino;

$R_2$ is OH, $C_1$ to $C_{12}$ alkoxy, $C_1$ to $C_{12}$ substituted alkoxy, O-glucosyl, oxo, alkyl or imino;

$R_3$, $R_4$, $R_5$, $R_6$, $R_7$, A, B, C, D and E are each independently H, halogen, OH, $C_1$ to $C_{12}$ alkoxy, $C_1$ to $C_{12}$ substituted alkoxy, aryloxy, O-glucosyl, $C_1$ to $C_{12}$ allyl or $C_1$ to $C_{12}$ substituted alkyl;

wherein $R_1$ and $R_2$, or $R_1$ and $R_4$ may form together a lactone which is optionally substituted;

wherein the bonds between $C_3:C_7$, $C_4:C_5$, and $C_9:C_{10}$ may independently be double bonds or single bonds;

provided that at least one of $R_3$, $R_4$, $R_5$, $R_6$, $R_7$, A, B, C, D and E is a halogen; and provided that, if A is the only halogen in the compound, that A is not fluoro:

or a derivative of said formula, wherein the derivative has at least one of the following:

a lower acyl side chain at $C_3$ (free acid or ester or conjugate), a keto or hydroxy (free hydroxy or ester) moiety at the $C_6$ carbon, or an n-pentenyl or n-pentyl side chain at $C_7$;

including salts, hydrates, solvates, polymorphs, optical isomers, enantiomers, diastereomers, and mixtures thereof.

More specifically, the preferred compounds of the present invention (Formula I) are those where the bond between $C_9$ and $C_{10}$ is a single bond. Other preferred compounds are where $R_2$ is oxo. Still other preferred compounds are where at least one of $R_6$ and $R_7$ is bromo, iodo, fluoro or chloro. Even more preferred are compounds where both of $R_6$ and $R_7$ are selected from bromo, iodo, fluoro or chloro. Yet more preferred are compounds where both of $R_6$ and $R_7$ are bromo.

A further preferred aspect of the invention are compounds where A, B, $R_6$ and $R_7$ are bromo, iodo, fluoro or chloro. Even more preferred are compounds where A, B, $R_6$ and $R_7$ are each bromo.

Other preferred compounds of the present invention are where $R_1$ is alkoxy. In yet another aspect, $R_3$, $R_4$ and $R_5$ are each (hydrogen). In still another aspect, C, D and E are each H.

One of the most preferred compounds of the present invention is methyl jasmonate di-bromide (MJDB). According to Formula I, MJDB is where: n is 0; the bonds between $C_3:C_7$, $C_4:C_5$, and $C_9:C_{10}$ are single bonds; $R_1$ is methoxy; $R_2$ is oxo; $R_3$, $R_4$, $R_5$, A, B, C, D and E are each H; and $R_6$ and $R_7$ are each bromo.

Another of the most preferred compounds of the present invention is methyl jasmonate tetra-bromide (MJTB). According to Formula I, MJTB is where: n is 0; the bonds between $C_3:C_7$, $C_4:C_5$, and $C_9:C_{10}$ are single bonds; $R_1$ is methoxy; $R_2$ is oxo; $R_3$, $R_4$, $R_5$, C, D and E are each H; and A, B, $R_6$ and $R_7$ are each bromo.

In other preferred compounds of the invention ii is 0; the bonds between $C_3:C_7$, $C_4:C_5$, and $C_9:C_{10}$ are single bonds; $R_1$ is methoxy; $R_2$ is oxo; $R_3$, $R_4$, $R_5$, A, B, C, D and E are each H; and either:

a) $R_6$ and $R_7$ are each fluoro (designated as compound "MJS99");

b) $R_6$ and $R_7$ are each iodo (designated as compound "MJS85f14");

c) $R_6$ and $R_7$ are each chloro (designated as compound "MJS81f13");

d) one of $R_6$ and $R_7$ is bromo and the other is hydroxy (designated as compound "NJ-63); or e) one of $R_6$ and $R_7$ is iodo and the other is methoxy (designated as compound "MJS72f5).

The present invention also contemplates pharmaceutical compositions that include a pharmaceutically acceptable carrier and, as an active ingredient, the compounds of the invention, as described above. Preferred compositions have as an active ingredient MJDB or MJTB. Preferably, in the pharmaceutical composition the active ingredient is dissolved in any acceptable lipid carrier. Further, in accordance with a preferred embodiment of the present invention, the composition additionally comprises at least one other chemotherapeutic agent.

The present invention additionally provides a method for reduction of the growth of mammalian cancer cells, comprising applying to the cancer cells a therapeutically effective amount of a compound of the invention, as described herein Furthermore, the present invention provides a method for the treatment of cancer in warm-blooded vertebrates, especially cancer in mammals, comprising administering to the subject a pharmaceutical composition containing as an active ingredient a therapeutically effective amount of the compound of the invention, as described herein. The term "mammals" includes non-human mammals and humans.

It is to be understood that whenever the terms "treating or inhibiting a malignant cell proliferative disease or disorder", "treating or inhibiting a non-solid cancer", "treating or inhibiting a tumor" are used herein in the description and in the claims, they are intended to encompass tumor formation, primary tumors, tumor progression or tumor metastasis.

The term "reduction of growth" in relation to cancer cells, in the context of the present invention refers to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a more differentiated cell type to a less differentiated cell type; a deceleration in the neoplastic progress; or alternatively the slowing of the progression of the cancer cells from one stage to the next.

Reduction of growth of cancer cells may be utilized for the treatment of cancer by the administration, to an individual in need of such treatment, of a therapeutically effective amount of the compound of the present invention, as described herein.

In a preferred embodiment, the methods of the invention comprise the use of Formula I, wherein at least one of $R_6$ and $R_7$ is Br. In further preferred embodiments, the compound is MJDB or MJTB.

The present invention additionally discloses use of a composition of Formula I, as described above, for preparing a medicament for the treatment of cancer in mammals.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastasis, reduction in the number of new metastasis formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment. This term also encompasses prevention for prophylactic situations or for those individuals who are susceptible to contracting a tumor. The administration of the compounds of the present invention will reduce the likelihood of the individual contracting the disease. In preferred situations, the individual to whom the compound is administered does not contract the disease.

The term "cancer" in the context of the present invention includes all types of neoplasm whether in the form of solid or non-solid tumors, from all origins, and includes both malignant and premalignant conditions as well as their metastasis. In particular this term refers to: carcinoma, sarcoma, adenoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell and non-small cell lung carcinoma, bladder carcinoma, epithelial carcinoma, glioma, astrocyoma, medulloblastoma, craniopharyngioma, ependynoma, pinealoma, retinoblastoma, multiple myeloma, rectal carcinoma, cancer of the thyroid, head and neck cancer, brain cancer, cancer of the peripheral nervous system, cancer of the central nervous system, neuroblastoma, cancer of the endometrium, lymphoproliferative diseases, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, as well as metastasis of all the above.

More preferably, the cancer is selected from the group consisting of prostate cancer, breast cancer, skin cancer, colon cancer, lung cancer, pancreatic cancer, lymphoma, leukemia, head and neck cancer, kidney cancer, ovarian cancer, bone cancer, liver cancer or thyroid cancer. Even more preferably, the cancer is selected from leukemia, including lymphoblastic leukemia, lung carcinoma, melanoma and colon cancer. Additionally, in a preferred embodiment of the method, the compound is administered at a dosage selected from 1 µg-1000 mg/kg body weight.

In other embodiments of the use of preparing a medicament, the medicament additionally comprises at least one active chemotherapeutic agent other than the compound of Formula I. In certain embodiments, the novel compound may be administered alongside with traditional chemotherapeutic drugs that are effective but have considerable side effects. The combination of a compound of the invention and the traditional drug may allow administration of a lesser quantity of the traditional drug, and thus the side effects experienced by the subject may be significantly lower, while a sufficient chemotherapeutic effect is nevertheless achieved.

The present invention additionally discloses a method for the treatment of cancer in a subject in need thereof, comprising administering to a mammal a therapeutically effective amount of a pharmaceutical composition comprising as the active ingredient a compound of the present invention, as described above.

There is also provided in the present invention a pharmaceutical composition for the treatment of cancer in mammals, comprising as the active ingredient a therapeutically effective amount of a compound of the invention, as described above, The invention also provides use of the compounds of the invention in the preparation of a medicament for reducing the growth of cancer cells, as described herein.

The present invention further discloses a method for preparation of MJDB

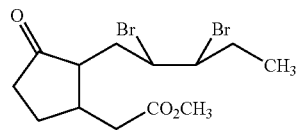

or MJTB

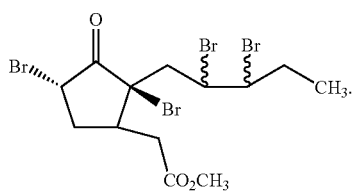

comprising:
i. adding bromine to a solution of methyl jasmonate in $CCl_4$; and
ii. evaporating the $CCl_4$.

Other jasmonate derivatives of the invention can be made, as described in the examples below. As further illustrations, an alkyl moiety can be added at the $R_2$ position, for example, by using a Grignard reagent at low temperature.

In addition, a 9,10-epoxide can be obtained from methyl jasmonate using peroxy acid, This epoxide can react with a compound of the formula RMgX resulting in hydroxyl and alkyl at the 9 and 10 positions ($R_6$ and $R_7$, respectively). A substituted alkyl can be added in similar fashion.

Moreover, reacting this epoxide with a compound of the formula ROH or ArOH wherein R is alkyl and Ar is aryl under acidic or basic conditions can result in a hydroxyl and alkyloxy or aryloxy at the 9 and 10 positions ($R_6$ and $R_7$, respectively). Furthermore, preparing the 5,6-enamine of methyl jasmonate will allow for an alkyl at the $C_5$ position (position B). A substituted alkyl can be added in similar fashion.

There is also provided in the present invention a pharmaceutical composition for the treatment of cancer in mammals, comprising as the active ingredient a therapeutically effective amount of a compound of the invention, as described herein, and a pharmaceutically acceptable carrier.

The term "pharmaceutically acceptable" means approved by a regulatory agency of the Federal or a state government or listed in the U.S. Pharmacopeia or other generally recognized pharmacopeia for use in animals and, more particularly, in humans.

The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like.

The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned.

The compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of a compound of the invention, preferably in a substantially purified form, together with a suitable amount of carrier so as to provide the form for proper administration to the subject.

The carrier can be selected at times based on the desired form of the formulation. The carrier may also at times have the effect of the improving the delivery or penetration of the active ingredient to the target tissue, for improving the stability of the drug, for slowing clearance rates, for imparting slow release properties, for reducing undesired side effects etc. The carrier may also be a substance that stabilizes the formulation (e.g. a preservative), for providing the formulation with an edible flavor, etc.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Accordingly, the carrier may include additives, colorants, diluents, buffering agents, disintegrating agents, moistening agents, preservatives, flavoring agents, and pharmacologically compatible carriers. In addition, the carrier may be an adjuvant, which, by definition are substances affecting the action of the active ingredient in a predictable way.

Methods of introduction of a pharmaceutical composition comprising a compound of the invention include, but are not limited to, topical, intradermal, intramuscular, intraperitoneal, intravenous, subcutaneous, intranasal, epidural, ophthalmic, and oral routes. The compounds may be administered by any convenient route, for example by infusion or bolus injection, by absorption through epithelial linings (e.g., oral mucosa, rectal and intestinal mucosa, etc.), and may be administered together with other therapeutically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer, and formulation with an aerosolizing agent.

It may be desirable to administer the pharmaceutical composition of the invention locally to the area in need of treatment; this may be achieved by, for example, and not by way of limitation, local infusion during surgery topical application, e.g., in conjunction with a wound dressing after surgery, by injection, by means of a catheter, by means of a suppository, or by means of an implant, said implant being of a porous, non-porous, or gelatinous material. According to some preferred embodiments, administration can be by direct injection e.g., via a syringe, at the site of a tumor or neoplastic or pre-neoplastic tissue.

Pharmaceutical compositions suitable for oral administration may consist of (a) liquid solutions, where an effective amount of the active substance is dissolved in diluents, such as water, saline, natural juices, alcohols, syrups, etc.; (b) solid dosage forms such as capsules (e.g. the ordinary hard- or soft-shelled gelatin type containing, for example, surfactants, lubricants, and inert fillers), tablets, lozenges (wherein the active substance is flavored, such as with sucrose and acacia or tragacanth, or the active substance is in an inert base, such as gelatin and glycerin), and troches, each containing a predetermined amount of the active ingredient as solids or granules; (c) powders; (d) suspensions in an appropriate liquid; (e) suitable emulsions; (f) liposome formulation; and others.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols.

For directed internal topical applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to materials of the above type, a liquid carrier such as a fatty oil. In addition, dosage unit forms can contain various other materials which modify the physical form of the dosage unit, for example, coatings of sugar, shellac, or other enteric agents.

A compound of the present invention can be delivered in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In a preferred form, a compound of the invention is administered in combination with a biodegradable, biocompatible polymeric implant, which releases the compound over a controlled period of time at a selected site. Examples of preferred polymeric materials include polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla.). In yet another embodiment, a controlled release system can be placed in proximity of the therapeutic target, thus requiring only a fraction of the systemic dose.

At times, the active compound may be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

Furthermore, at times, the pharmaceutical compositions may be formulated for parenteral administration (subcutaneous, intravenous, intraarterial, or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art.

The amount of a compound of the invention that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. A preferred dosage will be within the range of 0.01-1000 mg/kg of body weight, more preferably, 0.1 mg/kg to 100 mg/kg and even more preferably 1 mg/kg to 10 mg/kg. Effective doses may be extrapolated from dose-response curves derived from in vitro or animal model test bioassays or systems.

A "therapeutic" treatment is a treatment administered to a subject who exhibits signs of pathology for the purpose of diminishing or eliminating those signs A "therapeutically effective amount" of a compound of the invention is that amount of compound which is sufficient to provide a beneficial effect to the subject to which the compound is administered.

Patients in need thereof may suffer from a disease such as cancer or may have been determined to have a greater susceptibility to such disease. Thus, the method of treatment according to the present invention includes both therapeutic and prophylactic utility.

A compound of the invention can be tested in vivo for the desired therapeutic or prophylactic activity as well as for determination of a therapeutically effective dosage. For example, such compounds can be tested in suitable animal model systems prior to testing in humans, including, but not limited to, rats, mice, chicken, cows, monkeys, rabbits, and the like. For in vivo testing, prior to administration to humans, any animal model system known in the art may be used.

When the above-described compounds include one or more chiral centers, the stereochemistry of such chiral centers can independently be in the R or S configuration, or a mixture of the two. The chiral centers can be further designated as R or S or R,S or d,D, l,L or d,l, D,L.

The term "$C_1$ to $C_{12}$ alkyl" denotes such radicals as methyl, ethyl, n-propyl, isopropyl, n-butyl, iso-butyl, sec-butyl, tert-butyl, amyl, tert-amyl, hexyl, heptyl, octyl, nonyl, decyl, undecyl, dodecyl and the like. Preferred "$C_1$ to $C_{12}$ alkyl" groups are methyl, ethyl, iso-butyl, sec-butyl and iso-propyl. Similarly, the term "$C_1$ to $C_{12}$ alkylene" denotes radicals of 1 to 12 carbons connected to two other parts in the compound.

The term "$C_1$ to $C_{12}$ substituted alkyl denotes groups that are substituted by one or more, and preferably one or two substituents selected from halogen, hydroxy, protected hydroxy, oxo, protected oxo, $C_3$ to $C_7$ cycloalkyl, phenyl, substituted phenyl, naphthyl, amino, protected amino, (monosubstituted)amino, protected (monosubstituted) amino, (disubstituted)amino, guanidino, protected guanidino, heterocyclic ring, substituted heterocyclic ring, imidazolyl, indolyl, pyrrolidinyl, $C_1$ to $C_{12}$ alkoxy. $C_1$ to $C_{12}$ acyl, $C_1$ to $C_{12}$ acyloxy, nitro, carboxy, protected carboxy, carbamoyl, carboxamide, protected carboxamide, N—($C_1$ to $C_{12}$ alkyl)carboxamide, protected N—($C_1$ to $C_{12}$ alkyl)carboxamide. N,N-di($C_1$ to $C_{12}$ alkyl)carboxamide, cyano, methylsulfonylamino, thiol, $C_1$ to $C_{10}$ alkylthio or $C_1$ to $C_{10}$ alkylsulfonyl groups. The substituted alkyl groups may be substituted once or more, and preferably once or twice, with the same or with different substituents. A preferred substitution is halo.

The term "protected oxo" denotes a carbon atom bonded to two alkoxy groups thereby forming an acyclic or cyclic acetal or ketal moiety. The term "$C_1$ to $C_{12}$ alkoxy" as used herein denotes groups such as methoxy, ethoxy, n-propoxy, isopropoxy, n-butoxy, t-butoxy and like groups. A preferred alkoxy is methoxy. The term "$C_1$ to $C_{12}$ substituted alkoxy" means the alkyl portion of the alkoxy can be substituted in the same manner as in relation to $C_1$ to $C_{12}$ substituted allyl. A preferred substitution is halo. Similarly, the term "$C_1$ to $C_{12}$ phenylalkoxy" as used herein means "$C_1$ to $C_{12}$ alkoxy" bonded to a phenyl radical.

The term "$C_1$ to $C_{12}$ acyloxy" denotes herein groups such as formyloxy, acetoxy, propionyloxy, butyryloxy, pivaloyloxy, pentanoyloxy; hexanoyloxy, heptanoyloxy, octanoyloxy, nonanoyloxy, decanoyloxy, undecanoyloxy, dodecanoyloxy and the like.

Similarly, the term "$C_1$ to $C_{12}$ acyl" encompasses groups such as formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Preferred acyl groups are acetyl and benzoyl.

The term "$C_1$ to $C_{12}$ substituted acyl" denotes the acyl group substituted by one or more, and preferably one or two, of the substituents defined above for alkyl. The substituent term "$C_3$ to $C_7$ cycloalkyl" includes the cyclopropyl, cyclobutyl, cyclopentyl, cyclohexyl or cycloheptyl rings. Similarly, a substituent that can be $C_3$ to $C_7$ cycloalkyl" can also be "$C_5$ to $C_7$ cycloalkyl," which includes the cyclopentyl, cyclohexyl or cycloheptyl rings.

The substituent term "$C_3$ to $C_7$ substituted cycloalkyl" or "$C_5$ to $C_7$ substituted cycloalkyl" indicates the above cycloalkyl rings substituted by one or two of the substituents defined above for alkyl. The term "cycloalkylene" means a cycloalkyl, as defined above, where the cycloalkyl radical is bonded at two positions connecting together two separate additional groups. Similarly, the term "substituted cycloalkylene" means a cycloalkylene where the cycloalkyl radical is bonded at two positions connecting together two separate additional groups and further bearing at least one additional substituent.

Similarly, the term "substituted $C_5$ to $C_7$ cycloalkenylene" means a cycloalkenylene further substituted by halogen, hydroxy, protected hydroxy, $C_1$ to $C_{10}$ alkylthio, $C_1$ to $C_{10}$ alkylsulfoxide, $C_1$ to $C_{10}$ alkylsulfonyl, $C_1$ to $C_{10}$ substituted alkylthio, $C_1$ to $C_{10}$ substituted alkylsulfoxide, $C_1$ to $C_{10}$ substituted alkylsulfonyl, $C_1$ to $C_{12}$ alkyl, $C_1$ to $C_{12}$ alkoxy, $C_1$ to $C_{12}$ substituted alkyl, $C_1$ to $C_{12}$ alkoxy, oxo, protected oxo, (monosubstituted)amino, (disubstituted)amino, trifluoromethyl, carboxy, protected carboxy, phenyl, substituted phenyl, phenylthio, phenylsulfoxide, phenylsulfonyl, amino, or protected amino group.

The term "heterocycle" or "heterocyclic ring" denotes optionally substituted five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings may be saturated, fully unsaturated or partially unsaturated, with fully saturated rings being preferred. Preferred heterocyclic rings include morpholino, piperidinyl, piperazinyl, 2-amino-imidazoyl, tetrahydrofurano, pyrrolo, tetrahydrothiophenyl, hexylmethyleneimino and heptylmethyleneimino.

The term "substituted heterocycle" or "substituted heterocyclic ring" means the above-described heterocyclic ring is substituted with, for example, one or more, and preferably one or two, of the substituents defined above for alkyl. The term "heteroaryl" means a heterocyclic aromatic derivative which is a five-membered or six-membered ring system having from 1 to 4 heteroatoms, such as oxygen, sulfur and/or nitrogen, in particular nitrogen, either alone or in conjunction with sulfur or oxygen ring atoms. Examples of heteroaryls include pyridinyl, pyrimidinyl, and pyrazinyl pyridazinyl, pyrrolo, furano, oxazolo, isoxazolo, phthalimido, thiazolo and the like;

The term "substituted heteroaryl" means the above-described heteroaryl is substituted with, for example, one or more, and preferably one or two, substituents which are the same or different, of the substituents defined above for alkyl. The term "substituted phenyl" specifies a phenyl group substituted with one or more, and preferably one or to, moieties chosen from the substituents defined above for alkyl.

The term "phenoxy" denotes a phenyl bonded to an oxygen atom, wherein the binding to the rest of the molecule is through the oxygen atom. The term "substituted phenoxy" specifies a phenoxy group substituted with one or more, and preferably one or two, moieties chosen from the substituents defined above for alkyl.

The term "aryl" refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. The term "aryloxy" refers to an "aryl" group bonded to an oxygen atom, wherein the binding to the rest of the molecule is through the oxygen atom.

The terms "halo" and "halogen" refer to the fluoro, chloro, bromo or iodo atoms. There can be one or more halogens, which are the same or different.

The term "(monosubstituted) amino" refers to an amino group with one substituent chosen from the group consisting of phenyl, substituted phenyl, $C_1$ to $C_{12}$ alkyl, $C_1$ to $C_{12}$ substituted alkyl $C_1$ to $C_{12}$ acyl, $C_1$ to $C_{12}$ substituted acyl, $C_2$ to $C_{12}$ alkenyl, $C_2$ to $C_{12}$ substituted alkenyl, $C_2$ to $C_{12}$ alkynyl, $C_2$ to $C_{12}$ substituted alkynyl, $C_7$ to $C_{18}$ phenylalkyl, $C_7$ to $C_{18}$ substituted phenylalkyl, heterocyclic ring, substituted heterocyclic ring, $C_1$ to $C_{12}$ heterocycloalkyl and $C_1$ to $C_{12}$ substituted heterocycloalkyl. The (monosubstituted)amino can additionally have an amino-protecting group as encompassed by the term "protected (monosubstituted)amino".

The term "(disubstituted)amino" refers to an amino group with two substituents chosen from the group consisting of phenyl, substituted phenyl, $C_1$ to $C_{12}$ allyl, $C_1$ to $C_{12}$ substituted alkyl, $C_1$ to $C_{12}$ acyl, $C_2$ to $C_{12}$ alkenyl, $C_2$ to $C_{12}$ alkynyl, $C_7$ to $C_{15}$ phenylalkyl, $C_7$ to $C_{18}$ substituted phenylalkyl, $C_1$ to $C_{12}$ heterocycloalkyl and $C_1$ to $C_{12}$ substituted heterocycloalkyl. The two substituents can be the same or different.

The term "amino-protecting group" as used herein refers to substituents of the amino group commonly employed to block or protect the amino functionality while reacting other functional groups of the molecule. The term "protected (monosubstituted)amino" means there is an amino-protecting group on the monosubstituted amino nitrogen atom. In addition, the term "protected carboxamide" means there is an amino-protecting group on the carboxamide nitrogen. Similarly, the term "protected N—($C_1$ to $C_{12}$ alkyl)carboxamide" means there is an amino-protecting group on the carboxamide nitrogen.

The species of amino-protecting group employed is not critical so long as the derivatized amino group is stable to the conditions of the subsequent reaction(s) and can be removed at the appropriate point without disrupting the remainder of the compounds. Preferred amino-protecting groups are Boc, Cbz and Fmoc. Further examples of amino-protecting groups embraced by the above term are well known in organic synthesis and the peptide art and are described by, for example, T. W. Greene and P. G. M. Wuts, "Protective Groups in Organic Synthesis," 2nd ed., John Wiley and Sons, New York. N.Y., 1991, Chapter 7, M. Bodanzsky, "Principles of Peptide Synthesis," 1st and 2nd revised ed., Springer-Verlag, New York, N.Y., 1984 and 1993, and Stewart and Young, "Solid Phase Peptide Synthesis," 2nd ed., Pierce Chemical Co., Rock-ford, Ill. 1984, each of which is incorporated herein by reference. The related term "Protected amino" defines an amino group substituted with an amino-protecting group discussed above.

The term "protected guanidino" as used herein refers to an "amino-protecting group" on one or two of the guanidino nitrogen atoms, Examples of "protected guanidino" groups are described by T. W. Greene and P. G. M. Wuts; M. Bodanzsky; and Stewart ad Young, supra.

The term "thio" refers to —SH or, if between two other groups, —S—. The term "$C_1$ to $C_{10}$ alkylene thio" refers to a one to ten carbon alkylene chain with a thio at any point along the chain. The term "$C_1$ to $C_{10}$ substituted alkylene thio" refers to a $C_1$ to $C_{10}$ alkylene thio group that is substituted at one or more of the alkylene positions (in the same way as "substituted alkylene," as described above).

The term "sulfonyl" refers to —S(O)$_2$—. The term "$C_1$ to $C_{10}$ alkylene sulfonyl" refers to a one to ten carbon alkylene chain with a sulfonyl at any point along the chain. The term "$C_1$ to $C_{10}$ substituted alkylene sulfonyl" refers to a $C_1$ to $C_{10}$ alkylene sulfonyl group that is substituted at one or more of the alkylene positions (in the same way as "substituted allylene," as described above).

The term "sulfinyl" refers to —S(O)—. The term "$C_1$ to $C_{10}$ allylene sulfinyl" refers to a one to ten carbon alkylene chain with a sulfinyl at any point along the chain. The term "$C_1$ to $C_{10}$ substituted alkylene sulfinyl" refers to a $C_1$ to $C_{10}$ alkylene sulfinyl group that is substituted at one or more of the alkylene positions (in the same way as "substituted alkylene," as described above).

The term "oxy" refers to —O—. The terms "$C_1$ to $C_{10}$ allylene oxy," "$C_1$ to $C_{10}$ alkylene dioxy" and "$C_1$ to $C_{10}$ alkylene trioxy" refer to a one to ten carbon alkylene chain with, respectively, one, two or three —O— at any point along the chain, provided that no two oxygen atoms are consecutive, and provided that any two oxygen atoms are separated by at least two carbons. The terms "$C_1$ to $C_{10}$ substituted alkylene oxy," "$C_1$ to $C_{10}$ substituted allylene dioxy" and "$C_1$ to $C_{10}$ substituted alkylene trioxy" refer, respectfully to "$C_1$ to $C_{10}$ alkylene oxy," "$C_1$ to $C_{10}$ alkylene dioxy" and "$C_1$ to $C_{10}$ alkylene trioxy" that are substituted at one or more of the alkylene positions (in the same way as "substituted alkylene," as described above).

The term "carboxy-protecting group" as used herein refers to one of the ester derivatives of the carboxylic acid group commonly employed to block or protect the carboxylic acid group while reactions are carried out on other functional groups on the compound. Examples of these groups are found in E. Haslam, "Protective Groups in Organic Chemistry." J. G. W. McOmie, Ed., Plenum Press, New York N.Y., 1973, Chapter 5, and T. A. Greene and P. G. M. Wuts, "Protective Groups in Organic Synthesis," 2nd Pd, John Wiley and Sons, New York, N.Y., 1991, Chapter 5, each of which is incorporated herein by reference. A related term is "protected carboxy," which refers to a carboxy group substituted with one of the above carboxy-protecting groups.

The term "hydroxy-protecting group" refers to readily cleavable groups) bonded to hydroxyl groups. The species of hydroxy-protecting groups is not critical so long as the derivatized hydroxyl group is stable to the conditions of subsequent reaction(s) and can be removed at the appropriate point without disrupting the remainder of the molecule. Examples of hydroxy-protecting groups are described by C. B. Reese and E. Haslam "Protective Groups in Organic Chemistry," J. G. W. McOmie. Ed. Plenum Press. New York, N.Y., 1973, Chapters 3 and 4, respectively, and T. W. Greene and P. G. M. Wuts, "Protective Groups in Organic Synthesis," 2nd ed., John Wiley and Sons, New York, N.Y., 1991, Chapters 2 and 3. Related terms are "protected hydroxy," and "protected hydroxymethyl" which refer to a hydroxy or hydroxymethyl substituted with one of the above hydroxy-protecting groups.

The term "$C_1$ to $C_{10}$ alkylthio" refers to sulfide groups such as methylthio, ethylthio, n-propylthio, isopropylthio, n-butylthio, t-butylthio and like groups.

The term "$C_1$ to $C_{10}$ alklylsulfoxide" indicates sulfoxide groups such as methylsulfoxide, ethylsulfoxide, n-propylsulfoxide, isopropylsulfoxide, n-butylsulfoxide, sec-butylsulfoxide and the like. The term "$C_1$ to $C_{10}$ alkylsulfonyl" encompasses groups such as methylsulfonyl, ethylsulfonyl, n-propylsulfonyl, isopropylsulfonyl, n-butylsulfonyl, t-butylsulfonyl and the like. it should also be understood that the above thio, sulfoxide or sulfonyl groups can be at any point on the alkyl chain (e.g., 2-methylmercaptoethyl).

The terms "$C_1$ to $C_{10}$ substituted alkylthio," "$C_1$ to $C_{10}$ substituted alkylsulfoxide," and "$C_1$ to $C_{10}$ substituted alkylsulfonyl." denote the $C_1$ to $C_{10}$ alkyl portion of these groups may be substituted as described above in relation to "substituted alkyl."

The terms "phenylthio," "phenylsulfoxide," and "phenylsulfonyl" specify a thiol, a sulfoxide, or sulfone, respectively, containing a phenyl group. The terms "substituted phenylthio," "substituted phenylsulfoxide," and "substituted phenylsulfonyl" means that the phenyl of these groups can be substituted as described above in relation to "substituted phenyl."

The term "$C_1$ to $C_{12}$ alkylaminocarbonyl" means a $C_1$ to $C_{12}$ alkyl attached to a nitrogen of the aminocarbonyl group. Examples of $C_1$ to $C_{12}$ alkylaminocarbonyl include methylaminocarbonyl, ethylaminocarbonyl, propylaminocarbonyl and butylaminocarbonyl. The term "$C_1$ to $C_{12}$ substituted alklylaminocarbonyl" denotes a substituted alkyl bonded to a nitrogen of the aminocarbonyl group, which alkyl may be substituted as described above in relation to $C_1$ to $C_{12}$ substituted alkyl.

The term "$C_1$ to $C_{12}$ alkoxycarbonyl" means a "$C_1$ to $C_{12}$ alkoxy" group attached to a carbonyl group. The term "$C_1$ to $C_{12}$ substituted alkoxycarbonyl" denotes a substituted alkoxy bonded to the carbonyl group, which alkoxy may be substituted as described above in relation to "$C_1$ to $C_{12}$ substituted alkyl."

The term "phenylaminocarbonyl" means a phenyl attached to a nitrogen of the aminocarbonyl group. The term "substituted phenylaminocarbonyl" denotes a substituted phenyl bonded to a nitrogen of the aminocarbonyl group, which phenyl may be substituted as described above in relation to substituted phenyl.

The term "$C_1$ to $C_{12}$ alkylaminothiocarbonyl" means a $C_1$ to $C_{12}$ alkyl attached to an aminothiocarbonyl group, wherein the alkyl has the same meaning as defined above.

The term "$C_1$ to $C_{12}$ substituted alkylaminothiocarbonyl" denotes a substituted alkyl bonded to an aminothiocarbonyl group, wherein the alkyl may be substituted as described above in relation to $C_1$ to $C_{12}$ substituted alkyl.

The term "phenylaminothiocarbonyl" means a phenyl attached to an aminothiocarbonyl group, wherein the phenyl has the same meaning as defined above.

The term "substituted phenylaminothiocarbonyl" denotes a substituted phenyl bonded to an aminothiocarbonyl group, wherein phenyl may be substituted as described above in relation, to substituted phenyl.

The term "substituted $C_1$ to $C_{12}$ alkylene" means a $C_1$ to $C_{12}$ alkyl group where the alkyl radical is bonded at two positions connecting together two separate additional groups and further bearing an additional substituent.

The terms "cyclic $C_2$ to $C_7$ alkylene," "substituted cyclic $C_2$ to $C_7$ alkylene," "cyclic $C_2$ to $C_7$ heteroalkylene," and "substituted cyclic $C_2$ to $C_7$ heteroalkylene," defines such a cyclic group bonded ("fused") to the phenyl radical resulting in a bicyclic ring system. The cyclic group may be saturated or contain one or two double bonds. Furthermore, the cyclic group may have one or two methylene or methine groups replaced by one or two oxygen, nitrogen or sulfur atoms that are the cyclic $C_2$ to $C_7$ heteroalkylene.

The cyclic alkylene or heteroalkylene group may be substituted once or twice by the same or different substituents which, if appropriate, can be connected to another part of the compound (e.g., alkylene) selected from the group consisting of the following moieties: hydroxy, protected hydroxy, carboxy, protected carboxy, oxo, protected oxo, $C_1$ to $C_4$ acyloxy, formyl, $C_1$ to $C_{12}$ acyl, $C_1$ to $C_{12}$ alkyl $C_1$ to $C_7$ alkoxy, $C_1$ to $C_{10}$ alkylthio. $C_1$ to $C_{10}$ alkylsulfoxide $C_1$ to $C_{10}$ alkylsulfonyl, halo, amino, protected amino, (monosubstituted) amino, protected (monosubstituted)amino, (disubstituted) amino, hydroxymethyl or a protected hydroxymethyl.

The cyclic alkylene or heteroalkylene group fused onto the benzene radical can contain two to ten ring members, but it preferably contains three to six members. Examples of such saturated cyclic groups are when the resultant bicyclic ring system is 2,3-dihydro-indanyl and a tetralin ring. When the cyclic groups are unsaturated, examples occur when the resultant bicyclic ring system is a naphthyl ring or indolyl. Examples of fused cyclic groups which each contain one nitrogen atom and one or more double bond, preferably one or two double bonds, are when the benzene radical is fused to a pyridino, pyrano, pyrrolo, pyridinyl, dihydropyrrolo, or dihydropyridinyl ring. Examples of fused cyclic groups which each contain one oxygen atom and one or two double bonds are when the benzene radical ring is fused to a furo, pyrano, dihydrofurano, or dihydropyrano ring. Examples of fused cyclic groups which each have one sulfur atom and contain one or two double bonds are when the benzene radical is fused to a thieno, thiopyrano, dihydrothieno or dihydrothiopyrano ring. Examples of cyclic groups that contain two heteroatoms selected from sulfur and nitrogen and one or two double bonds are when the benzene radical ring is fused to a thiazolo, isothiazolo, dihydrothiazolo or dihydroisothiazolo ring. Examples of cyclic groups which contain two heteroatoms selected from oxygen and nitrogen and one or two double bonds are when the benzene ring is fused to an oxazolo, isoxazolo, dihydrooxazolo or dihydroisoxazolo ring. Examples of cyclic groups which contain two nitrogen heteroatoms and one or two double bonds occur when the benzene ring is fused to a pyrazolo, imidazolo, dihydropyrazolo or dihydroimidazolo ring or pyrazinyl.

The term "carbamoyl" means an —NC(O)— group where the radical is bonded at two positions connecting two separate additional groups.

One or more of the compounds of the invention, may be present as a salt. The term "salt" encompasses those salts that form with the carboxylate anions and amine nitrogens and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicyclic, methanesulfonic, benzenesulfonic, sorbic, picric, benzoic, cinnamic, and like acids.

The term "organic or inorganic cation" refers to counter-ions for the carboxylate anion of a carboxylate salt. The counter-ions are chosen from the alkali and alkaline earth metals, (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, "Pharmaceutical Salts," Berge et al., J. Pharm. Sci., 66:1-19 (1977), which is incorporated herein by reference. Other cations encompassed by the above term include the protonated form of procaine, quinine and N-methylglucosamine, and the protonated forms of basic amino acids such as glycine, ornithine, histidine, phenylglycine, lysine and arginine. Furthermore, any zwitterionic form of the instant compounds formed by a carboxylic acid and an amino group is referred to by this term. For example, a cation for a carboxylate anion will exist when a position is substituted with a (quaternary ammonium) methyl group. A preferred cation for the carboxylate anion is the sodium cation.

The compounds of the invention can also exist as solvates and hydrates. Thus, these compounds may crystallize with, for example, waters of hydration, or one, a number of, or any fraction thereof of molecules of the mother liquor solvent. The solvates and hydrates of such compounds are included within the scope of this invention.

One or more compounds of the invention, even when in a library, can be in the biologically active ester form, such as the non-toxic, metabolically-labile ester-form. Such ester forms induce increased blood levels and prolong the efficacy of the corresponding non-esterified forms of the compounds. Ester groups which can be used include the lower alkoxymethyl groups, for example, methoxymethyl, ethoxymethyl, isopropoxymethyl and the like; the —($C_1$ to $C_{12}$) alkoxyethyl groups, for example methoxyethyl, ethoxyethyl, propoxyethyl, isopropoxyethyl and the like; the 2-oxo-1,3-diooxlen-4-ylmethyl groups, such as 5-methyl-2-oxo-1,3-dioxolen-4-ylmethyl, 5-phenyl-2-oxo-1,3-dioxolen-4-ylmethyl and the like: the $C_1$ to $C_{10}$ alkylthiomethyl groups, for example methylthiomethyl, ethylthiomethyl, iso-propylthiomethyl and the like; the acyloxymethyl groups, for example pivaloyloxymethyl, pivaloyloxyethyl, -acetoxymethyl and the like; the ethoxycarbonyl-1-methyl group; the -acetoxyethyl; the 1-($C_1$ to $C_{12}$ alkyloxycarbonyloxy)ethyl groups such as the 1-(ethoxycarbonyloxy)ethyl group; and the 1-($C_1$ to $C_{12}$ allklaminocarbonyloxy)ethyl groups such as the 1-(methylaminocarbonyloxy)ethyl group.

It should be understood that any position of the claimed invention has up to three serial "substitutions." For example, a "substituted alkyl" that is substituted with a "substituted phenyl" that is, in turn, substituted with a "substituted alkyl" can, in turn, be substituted by one more group and no longer further substituted. However, it should also be understood that the invention contemplates, if appropriate, more than three parallel substitutions. For example, if appropriate, more than three hydrogens on an alkyl moiety may be substituted with any one or more of a variety of groups, including halo and hydroxy.

EXAMPLES

Experimental Procedures

Synthesis of MJDB

A solution of methyl jasmonate in $CCl_4$ at −20° C. was treated with bromine until a yellow color was kept for 5 minutes. The solvent was then evaporated and the yellowish residue chromatographed on an MeOH washed Silica gel column (VLC) and eluted with hexane/5-10% EtOAc.

A 1:1 mixture of two possible racemates was obtained.

Mass spectra: m/z 384 ($Br_2$), Rf=0.8 on silica gel eluted with hexane/EtOAc 1:1. C NMR (CDCl3): (C-1 to C-13): 172.11/172.3; 37.1/373; 38.0/38; 29.5/29.6; 38.8/39.1; 218.4/219.1; 51.7 (for both); 27.0/27.2; 57.8/55.8; 60.7/60.2; 35.7/36.1; 12.4 (for both). 51.1/51.3 ppm. H NMR (CDCl3): 2.39-2.41 (H-2 and 3); 1.94-2.14 (H-4, H-7 and H-11); 2.74-2.75 (H-5); 1.61 (H-8) 4.62 and 4.89 (H-9); 4.14 (H-10) 1.12 (H-12); 3.75 (OMe) ppm.

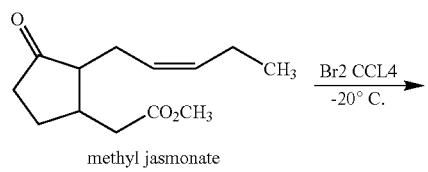

methyl jasmonate

-continued

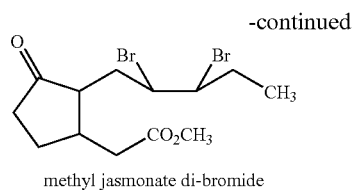

methyl jasmonate di-bromide

Synthesis of MJTB

MJ in CCl4 was treated over night with 10 equivalents of bromine. The solvent and excess of bromine were evaporated under vacuum. Recrystallizations from iPrOH gave one tetra bromo isomer and recrystallizations from EtOH gave a second isomer. The compounds were identified by NMR, MS and one isomer by an X-ray diffraction analysis.

Synthesis Of MJS72f5

To a stirred solution of (±)-MJ (111 mg, 0.49 mmol) in methanol (5 mL) at 0° C. was added dropwise a solution of $I_2$ (580 mg. 2.28 mmol) in methanol (15 mL). The mixture was stirred for 0.5 hr at 0° C. in the dark allowed to warm up to room temperature and then stirred further for 48 hr. The solvent was then evaporated, saturated aq. $Na_2SO_3$ (10 mL) was added to the residue, and extracted with ether (2×10 mL). The combined organic layer was dried over $MgSO_4$ and concentrated in vacuo. The residue was purified by VLC (EtOAc/petroleum ether 1:4) affording the product (42 mg, 22%) as a colorless oil.

Synthesis of MJS99f7

Fluorine, at a concentration of 3% in $N_2$, was passed as a slow stream through a cold (−75° C.) and vigorously stirred solution of the substrate(±)-MJ (2.1 gr, 9.37 mmol) dissolved in 250 mL of $CFCl_3$, 200 mL of $CHCl_3$, and 50 mL of ethanol. The reaction was carried out for 3 hr. then the mixture was poured into 500 mL of water, washed with saturated aq. $NaHCO_3$ and extracted with $CH_2Cl_2$. The combined organic layer was dried over $MgSO_4$ and concentrated in vacuo. The residue was purified by VLC (EtOAc/petroleum ether 1:9) affording a mixture of diastereomers (950 mg, 39%) as a red oil.

Synthesis of MJS85f4

To a stirred solution of (±)-MJ (246 mg, 1.10 mmol) in dry THF (6 mL) at 0° C. was added dropwise a solution of $I_2$ (1.17 gr, 4.6 mmol) in THF (15 mL). The mixture was stirred for 3 hr at 0° C. in the dark, allowed to warm up to room temperature and then stirred further for 48 hr. After completion, saturated aq. $Na_2SO_3$ (10 mL) was added to the residue, and extracted with ether (2×10 mL). The combined organic layer was dried over $MgSO_4$ and concentrated in vacuo. The residue was purified by VLC (EtOAc/petroleum ether 1:4) affording iodination products.

Synthesis OF MJS81f3

To a stirred solution of (±)-MJ (78 mg, 0.349 mmol) in $CCl_4$ (5 mL) at −10° C. was bubbled $Cl_2$ that was made in situ from concentrated HCl (5 mL) and $KMnO_4$ (800 mg). The mixture was stirred at −10° C. for 2 hr. The solvent was then evaporated and the residue purified by VLC (EtOAc/petroleum ether 1:19) affording chlorination products.

Cytotoxicity Assay Used in Examples

Measurement of reduction in the number of living cells was determined by, the CellTiter 96 Aqueous Non-Radioactive Cell Proliferation Assay (Promega, Madison Wis.). Upon completion of a given experiment, MTS (a tetrazolium compound) at 333 μg/ml+phenazine methosulfate (at 25 μM) was added to each well of the 96-well plate for 1 hour at 37° C. This allowed for development of a color reaction in which dehydrogenases reduce the MTS in metabolically active cells. Since the cells were not washed before the addition of MTS, there were no potentially loosely adherent or non-adherent cells that could have been problematic. Soluble MTS formazan product was measured at a wavelength of 490 nm using a CERES 900 HDI ELISA reader (Bio-Tek Instruments, Inc, Highland Park, Vt.), Optical density is directly proportional to the number of living cells in culture. Cytotoxicity (%) was calculated in the following way: [(OD of control cells−OD of drug-treated cells)/OD of control cells]×100.

Example 1

MJDB is Highly Cytotoxic Towards Leukemia Cells, and Non-toxic Towards Healthy Lymphocytes In order to test the toxicity of MJDB towards human leukemia cells, peripheral blood lymphocytes from chronic lymphocytic leukemia (CLL) patients were harvested. These cells were shown to contain practically 100% cancer cells, as determined by flow cytometric analysis of the CD5 and CD19 markers upon the cell surface. Peripheral blood lymphocytes from healthy donors were similarly harvested. Cells were seeded at $1.5×10^4$/well, in 96-well plates and MJDB was added for 1 day at several concentrations indicated in FIG. 1. The optical density that represented viable cells was determined by the CellTiter 96 Aqueous Non-Radioactive Cell Proliferation Assay (Promega, Madison, Wis.); an assay in which viable cells produce a colored product, as described above. This assay is quantitative, as the amount of color produced is read using an ELISA reader. Cytotoxicity was calculated as the % of control untreated cultures, mean±SD; n=3.

The cytotoxicity of MJDB towards peripheral blood lymphocytes from CLL patients was plotted versus its cytotoxicity towards peripheral blood lymphocytes from healthy donors (represented by diamonds). See FIG. 1. MJDB was clearly and significantly (P<0.05) more cytotoxic towards peripheral blood lymphocytes from chronic lymphocytic leukemia (CLL) patients than towards peripheral blood lymphocytes from healthy donors. MJDB is highly and selectively cytotoxic towards cancer cells from CLL patients, while cytotoxicity is minimal towards lymphocytes from healthy donors.

Example 2

MJDB is Far More Cytotoxic than Previously Studied Jasmonates, as Shown Against Four Diverse Human Malignant Cell Lines The cytotoxicity of MJDB was compared to that of the previously studied jasmonate, methyl jasmonate (MJ), which was the most effective jasmonate disclosed in U.S. Pat. No. 6,469,061. The cytotoxicity of these compounds was compared as seen when each was applied to four human malignant cell lines originating in lymphoblastic leukemia, lung carcinoma melanoma, or colon carcinoma.

Molt-4 lymphoblastic leukemia cells (at $1.5×10^4$/well), 3LL lung carcinoma cells (at $4×10^3$/well), B16 melanoma cells (at $4×10^3$/well), or HCT116 colon carcinoma cells (at $4×10^3$/well) were seeded in 96-well plates and methyl jasmonate (MJ) or MJDB at 0.5 mM were added for 1 day. Optical density representing viable cells was determined by the CellTiter 96 Aqueous Non-Radioactive Cell Proliferation Assay (described above). Cytotoxicity was calculated as the % of control untreated cultures, mean±SD. n=3.

Figure 2:
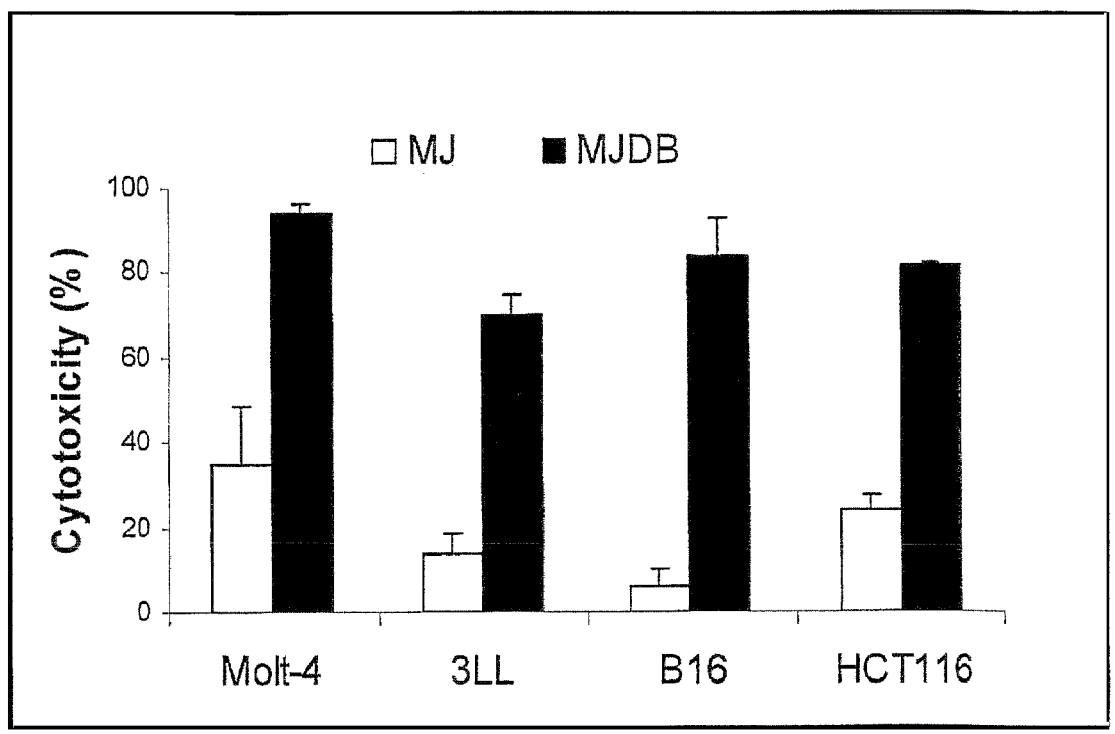
FIG. 2 shows a comparison of the level of toxicity effected by MJDB and by methyl jasmonate (MJ) on four human malignant cell lines: lymphoblastic leukemia (Molt-4), lung carcinoma (3LL), melanoma (B16) and colon carcinoma (HCT116).

The percentage of cytotoxicity of methyl jasmonate (MJ, white columns) or MJDB (filled columns) is illustrated. FIG. 2 clearly indicates that the newly synthesized compound MJDB is highly superior in its cytotoxic effect upon the various cancer cell lines, as compared to the previously studied methyl jasmonate. (Statistical studies showed P<0.05 for these results).

Example 3

MJDB is Effective Against Either Cells Expressing Wild Type or Mutant p53

The effect of MJDB towards cells expressing a mutated form of the pro-apoptotic tumor suppressor gene, p53, was shown. Aberrant p53 expression occurs in about 50% of human cancers and contributes to drug resistance and the ensuing failure of chemotherapy and irradiation in cancer patients. Consequently, the ability to kill mutant p53-expressing cells is of high clinical significance.

Figure 3:
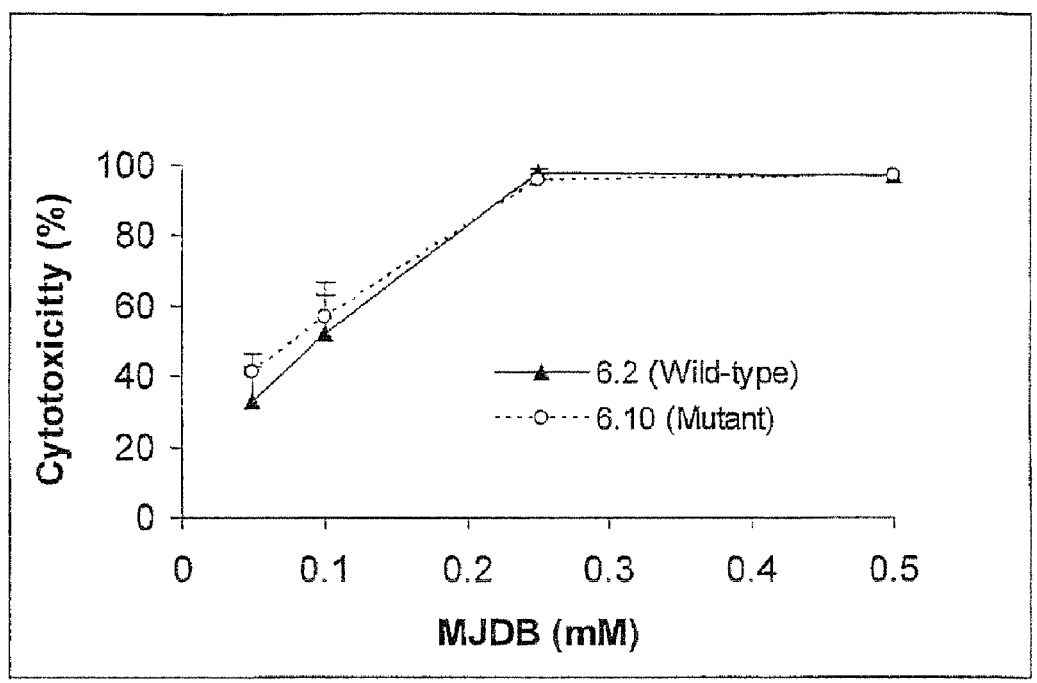
FIG. 3 shows the cytotoxic activity of MJDB, against cells expressing either wild type or mutant p53.

A system of two B lymphoma clones originating from the same cell line (29M4.1) was used. These clones differed solely in the expression of wild type versus mutant p53. More specifically, 29M4.1 cells were seeded at $2.5 \times 10^4$/well, in 96-well plates and MJDB were added for 1 day at several concentrations. The optical density that represented viable cells was determined by the CellTiter 96 Aqueous Non-Radioactive Cell Proliferation Assay (Promega, Madison, Wis.). Cytotoxicity was calculated as the percentage of control untreated cultures, mean±SD. n=3. MJDB was shown to be equally cytotoxic towards B lymphoma cells expressing either wild type or mutant p53, suggesting the potential clinical use of MJDB against drug resistant tumors. See FIG. 3.

Example 4

MJDB Lowers ATP Levels in Cancer Cells

An ATP determination assay was used to assess the effect of MJDB on ATP levels in cancer cells. More specifically, Molt-4 cells (at $1 \times 10^4$/well) were seeded in 96-well opaque-walled plates and MJ at 3 mM or MJDB at 1 mM were added for 10, 30 or 60 minutes at 37° C. Untreated cells incubated in culture medium were used as control. ATT levels were determined by the CellTiter-Glo™ Luminescent Cell Viability Assay; an assay in which cells produce a lumineascence signal that is equivalent to the ATP concentration in the cell. ATP depletion is calculated as % of control untreated cultures, mean±SD. n=3.

Figure 4:
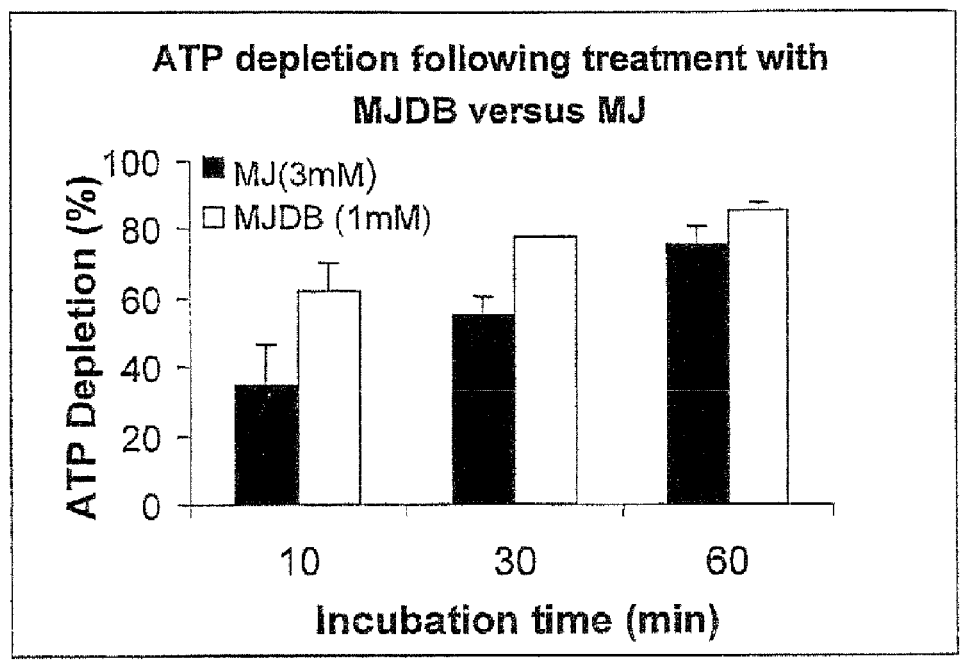
FIG. 4 shows a comparison of the effect of MJDB and MJ on ATP levels in Molt-4 leukemia cells.

As can be seen in FIG. 4, MJDB induced a rapid and strong ATP depletion in Molt-4 leukemia cells, to an extent bigger than that induced by methyl jasmonate. It is important to note that MJDB was administered at a 3 times lower concentration than methyl jasmonate. Thus, a correlation exists between the superior cytotoxic effect of MJDB (in comparison to methyl jasmonate) and its ability to reduce the cellular ATP levels.

Example 5

MJTB is Cytologic Against Four Diverse Human Malignant Cell Lines

Molt-4 (leukemia, at $2.5 \times 10^4$/ml), D122 (lung carcinoma, at $5 \times 10^3$/ml), B16 (melanoma, at $2 \times 10^3$/ml), and B16MDR (melanoma exhibiting multidrug resistance, at $2 \times 10^3$/ml) cells were incubated for one day in 96-well plates in the presence of different concentrations of MJTB. The optical density that represented viable cells was determined by the CellTiter 96 Aqueous Non-Radioactive Cell Proliferation Assay (Promega, Madison, Wis.), as described above. Cytotoxicity was calculated as % of control untreated cultures, mean±SE. n=3. The IC50 levels of MJTB against these cell lines are shown in the table below:

|  | Molt-4 | D122 | B16 | B16 MDR |
|---|---|---|---|---|
| IC50 (mM) | 0.008 | 0.05 | 0.08 | 0.08 |

Figure 5:
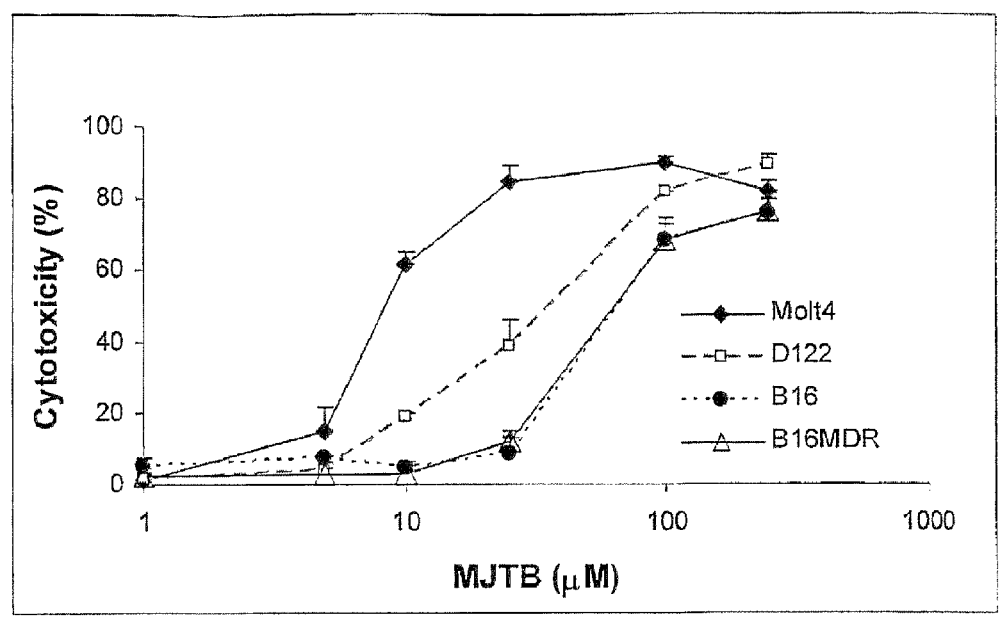
FIG. 5 shows the cytotoxic activity of MJTB against different cell lines: Molt4 (leukemia), D122 (lung carcinoma), B16 (melanoma) and B16MDR (melanoma exhibiting multidrug resistance.
Figure 6:
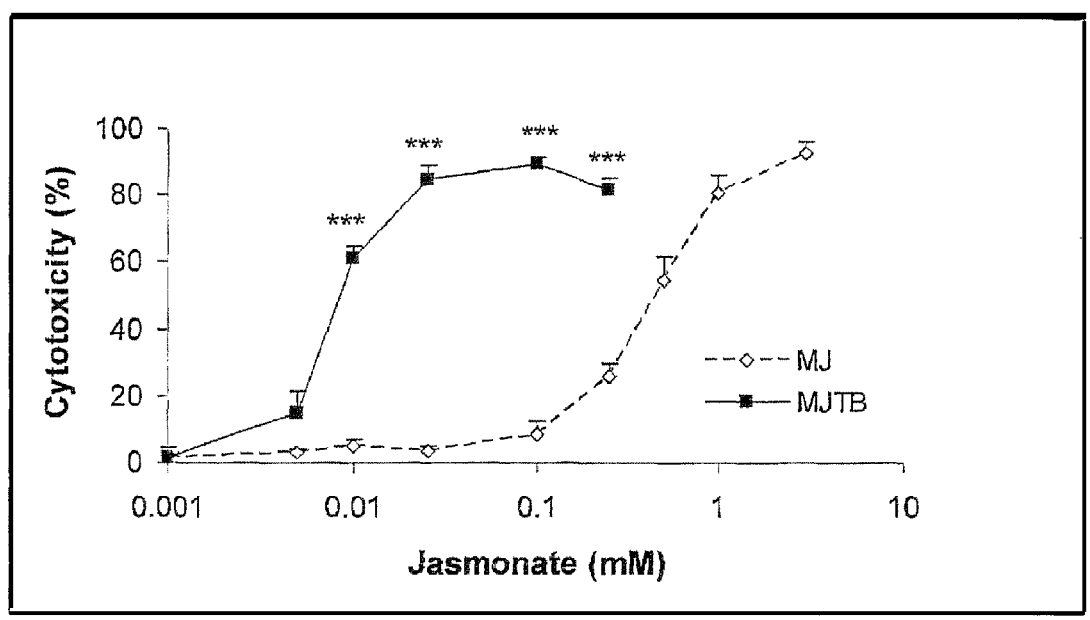
FIG. 6 compares the cytotoxic activity of MJTB and MJ. Cytotoxicity is calculated as % of control untreated cultures, mean±SE. n=3. *** denotes P<0.001 comparing the effects of MJ and MJTB.

As can be seen from this table and FIG. 5, MJTB was effective against both leukemic cells as well as cancer cells derived from various solid tumors. In addition, MJTB was capable of killing cells that express multidrug resistance, making it potentially useful in clinical situations where drug resistance is a major obstacle to successful chemotherapy.

Example 6

Comparison of MJ and MJTB

Biological assays were performed with a 1:1 mixture of the aforementioned tetra bromo isomers. More specifically, Molt-4 leukemic cells (at $2.5 \times 10^4$/ml) were incubated for one day in 96-well plates in the presence of different concentrations of either MJ or MJTB. The optical density that represented viable cells was determined by the CellTiter 96 Aqueous Non-Radioactive Cell Proliferation Assay (Promega, Madison, Wis.) as described above. Cytotoxicity is calculated as % of control untreated cultures, mean±SE. n=3. The IC50 levels of MJTB and MJ are shown in the table below:

|  | MJTB | MJ |
|---|---|---|
| IC50 (mM) | 0.008 | 0.5 |

As can be seen in this table and FIG. 5, MJTB has an IC50 (concentration exhibiting 50% cytotoxicity) that is about 60 times smaller than that of MJ (the most potent jasmonate derivative until now). Thus, MJTB is more effective than MJ by more than an order of magnitude.

Example 7

MJTB is Selective Against Cancer Cells

Molt-4 (leukemia) cells (at $2.5 \times 10^4$/ml), and normal peripheral blood lymphocytes (PBL, at $2 \times 10^5$/ml) were incubated in 96-well plates for one day in the presence of different concentrations of MJTB. PBL were pre-incubated with 0.8 µg/ml phytohaemagglutinin +5 ng/ml TPA for 48 hours, to induce entrance into the cell cycle. These cells proliferate and therefore are similar in that respect to cancer cells, making the comparison more valid. The optical density that represented viable cells was determined by the CellTiter 96 Aqueous Non-Radioactive Cell Proliferation Assay (Promega, Madison, Wis.), as described above. IC50 levels are shown in the table below:

|  | Molt-4 | PBL |
| --- | --- | --- |
| IC50 (mM) | 0.008 | 0.25 |

Figure 7:
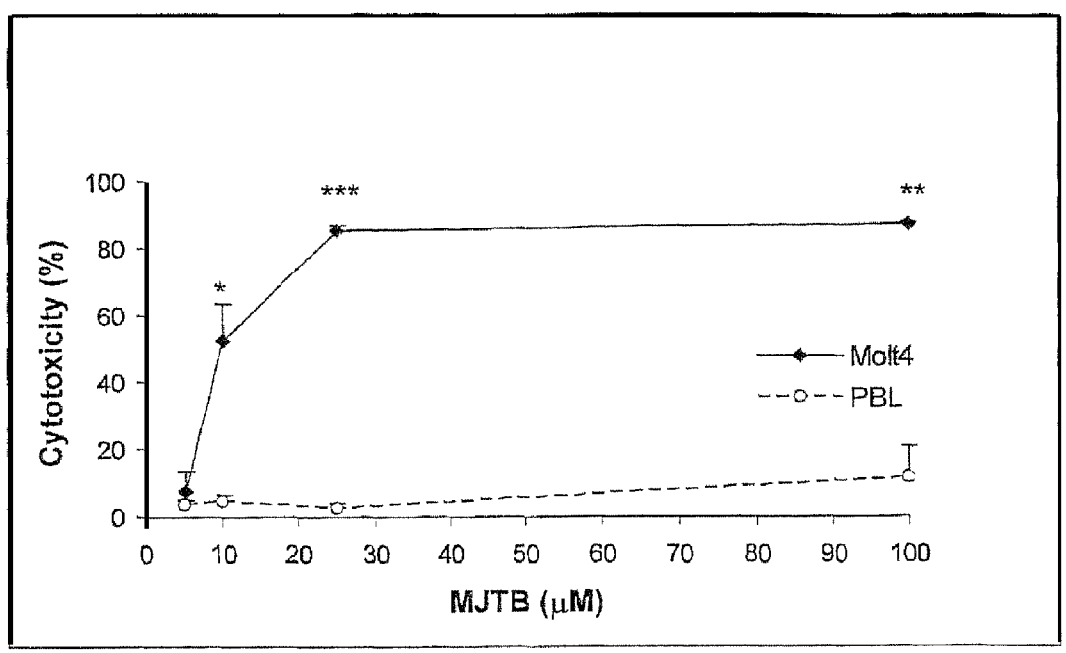
FIG. 7 compares the effect of MJTB on normal lymphocytes versus leukemic cells. * denotes P<0.05,  denotes P<0.01, * denotes P<0.001 comparing the effects of MJTB on leukemic versus normal lymphocytes. Cytotoxicity was calculated as % of control untreated cultures, mean±SE. n=3.

As can be seen in this table and FIG. 7, there is a comfortable therapeutic window which allows MJTB to kill leukemic cells without exerting a substantial effect on normal lymphocytes. Indeed, the IC50 for normal peripheral blood lymphocytes is larger than that for leukemic cells by more than an order of magnitude. It should be noted that the IC50 of PBL was determined using higher MJTB concentrations that do not appear in FIG. 7.

Example 8

Cytotoxicity of Other Compounds of the Invention

Figure 8:
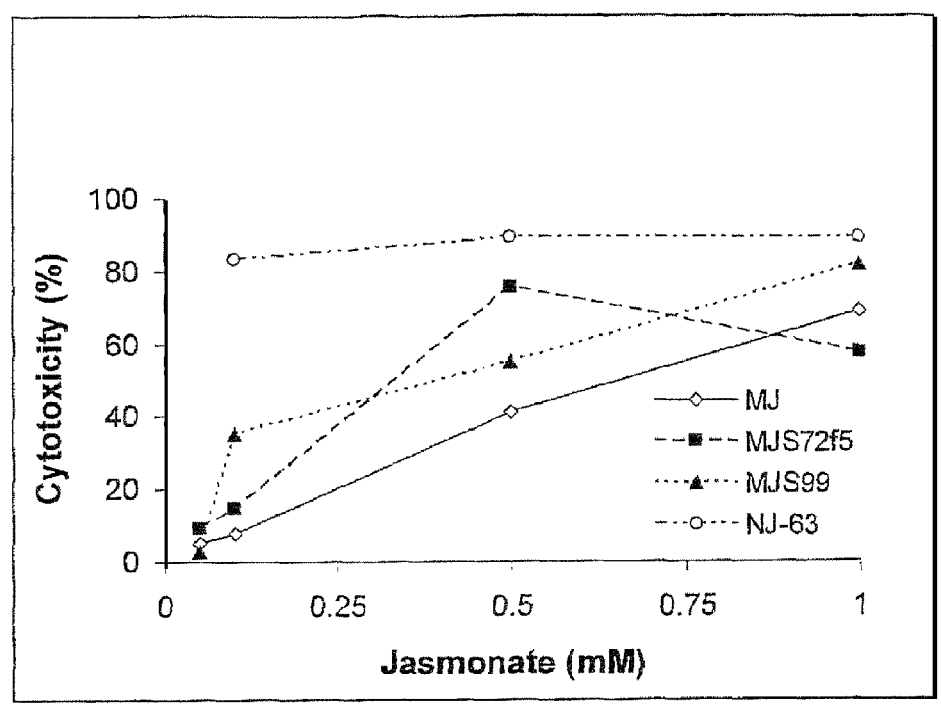
FIG. 8 shows the cytotoxicity of other MJ derivatives of the invention against leukemia cells.

Molt4 leukemic cells (at $1.5 \times 10^4$/ml) were incubated for 1 day in the presence of different concentrations of halogenated derivatives of MJ. Specifically, these derivatives were MJS72f5 (one of $R_6$ and $R_7$ is iodo and the other is methoxy), MJS99 ($R_6$ and $R_7$ are each fluoro) and NJ-63 (one of $R_6$ and $R_7$ is bromo and the other is hydroxyl). The optical density that represented viable cells was determined by the CellTiter 96 Aqueous Non-Radioactive Cell Proliferation Assay (Promega, Madison, Wis.), described above. As shown in FIG. 8, all of these derivatives showed greater cytotoxicity than MJ. Another derivative. MJS81f3, also had cytotoxic activity.

All references cited herein are incorporated in their entirety. It is appreciated that the detailed description herein above is intended only to illustrate certain preferred embodiments of the present invention. It is in no way intended to limit the scope of the inventions as set out in the claims that follow.

We claim:

1. A compound of Formula I:

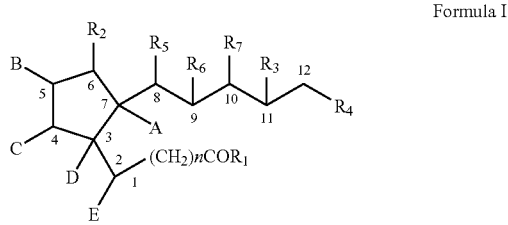

Formula I wherein:

n is 0;

$R_1$ is OH, $C_1$ to $C_{12}$ alkoxy, or $C_1$ to $C_{12}$ substituted alkoxy;

$R_2$ is oxo;

$R_3$, $R_4$, $R_5$, C, D and E are each H;

A and B are each H or halogen;

$R_6$ and $R_7$ are each selected from the group consisting of fluoro, chloro, bromo, iodo, hydroxy, $C_1$ to $C_{12}$ alkoxy, and $C_1$ to $C_{12}$ substituted alkoxy, provided that at least one of $R_6$ and $R_7$ is bromo, fluoro, chloro or iodo;

wherein the bonds between $C_3$:$C_7$, $C_4$:$C_5$, and $C_9$:$C_{10}$ may independently be double bonds or single bonds;

including salts, hydrates, optical isomers, enantiomers, diastereomers, and mixtures thereof.

2. The compound of claim 1, wherein
 (a) $R_6$ and $R_7$ are each bromo; or
 (b) $R_6$ and $R_7$ are each fluoro; or
 (c) $R_6$ and $R_7$ are each iodo; or
 (d) $R_6$ and $R_7$ are each chloro; or
 (e) one of $R_6$ and $R_7$ is bromo and the other is hydroxy, $C_1$ to $C_{12}$ alkoxy, or $C_1$ to $C_{12}$ substituted alkoxy; or
 (f) one of $R_6$ and $R_7$ is iodo and the other is methoxy.

3. The compound of claim 1, wherein the bond between $C_9$:$C_{10}$ is a single bond.

4. The compound of claim 3, wherein the bonds between $C_3$:$C_7$, $C_4$:$C_5$, and $C_9$:$C_{10}$ are single bonds.

5. The compound of claim 1, wherein the bond between $C_3$:$C_7$ is a single bond.

6. The compound of claim 1, wherein the bond between $C_3$:$C_7$ is a double bond.

7. The compound of claim 1, wherein $R_1$ is OH, methoxy, t-butoxy or substituted alkoxy.

8. The compound of claim 1, wherein: the bonds between $C_3$:$C_7$, $C_4$:$C_5$, and $C_9$:$C_{10}$ are single bonds; $R_1$ is methoxy; A and B are each H; and $R_6$ and $R_7$ are each fluoro.

9. The compound of claim 1, wherein: the bonds between $C_3$:$C_7$, $C_4$:$C_5$, and $C_9$:$C_{10}$ are single bonds; $R_1$ is methoxy; A and B are each H; and $R_6$ and $R_7$ are each iodo.

10. The compound of claim 1, wherein: the bonds between $C_3$:$C_7$, $C_4$:$C_5$, and $C_9$:$C_{10}$ are single bonds; $R_1$ is methoxy; A and B are each H; and $R_6$ and $R_7$ are each chloro.

11. The compound of claim 1, wherein: the bonds between $C_3$:$C_7$, $C_4$:$C_5$, and $C_9$:$C_{10}$ are single bonds; $R_1$ is methoxy; A and B are each H; $R_6$ is hydroxy and $R_7$ is bromo.

12. The compound of claim 1, wherein: the bonds between $C_3$:$C_7$, $C_4$:$C_5$, and $C_9$:$C_{10}$ are single bonds; $R_1$ is methoxy; A and B are each H; one of $R_6$ and $R_7$ is iodo and the other is methoxy.

13. A pharmaceutical composition comprising a pharmaceutically acceptable carrier, and as an active ingredient a compound of claim 1.

14. The pharmaceutical composition according to claim 13, wherein the composition is in a form suitable for topical administration.

15. The pharmaceutical composition according to claim 14, wherein the composition is in the form selected from the group consisting of an ointment, a cream, a gel, and drops.

16. A method for reduction of the growth of cancer cells, comprising exposing the cancer cells to a therapeutically effective amount of a compound of claim 1.

17. The method of claim 16, wherein the cancer is a mammalian cancer.

18. The method of claim 17, wherein the cancer is a human cancer.

19. The method of claim 16, wherein the cancer is selected from the group consisting of carcinoma, sarcoma, adenoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell and non-small cell lung carcinoma, bladder carcinoma, epithelial carcinoma, glioma, astrocyoma, medulloblastoma, craniopharyngioma, ependynoma, pinealoma, retinoblastoma, rectal carcinoma, cancer of the thyroid, head and neck cancer, brain cancer, cancer of the peripheral nervous system, cancer of the central nervous system, neuroblastoma, cancer of the endometrium, lymphoproliferative diseases, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

20. A method for the treatment of cancer comprising administering to the subject in need thereof a pharmaceutical composition containing as an active ingredient a therapeutically effective amount of the compound according to claim 1.

21. The method of claim 20, wherein the cancer is a mammalian cancer.

22. The method of claim 21, wherein the cancer is a human cancer.

23. The method according to claim 20, wherein the cancer is selected from the group consisting of carcinoma, sarcoma, adenoma, hepatocellular carcinoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, lymphagiosarcoma, synovioama, Ewing's tumor, leimyosarcoma, rhabdotheliosarcoma, colon carcinoma, pancreatic cancer, breast cancer, ovarian cancer, prostate cancer, squamous cell carcinoma, basal cell carcinoma, adenocarcinoma, renal cell carcinoma, hematoma, bile duct carcinoma, melanoma, choriocarcinoma, seminoma, embryonal carcinoma, Wilms' tumor, cervical cancer, testicular tumor, lung carcinoma, small cell and non-small cell lung carcinoma, bladder carcinoma, epithelial carcinoma, glioma, astrocyoma, medulloblastoma, craniopharyngioma, ependynoma, pinealoma, retinoblastoma, rectal carcinoma, cancer of the thyroid, head and neck cancer, brain cancer, cancer of the peripheral nervous system, cancer of the central nervous system, neuroblastoma, cancer of the endometrium, lymphoproliferative , hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, as well as metastasis of all the above.

24. The method of claim 20, wherein the cancer is selected from the group consisting of prostate cancer, breast cancer, skin cancer, colon cancer, lung cancer, pancreatic cancer, lymphoma, leukemia, head and neck cancer, kidney cancer, ovarian cancer, bone cancer, liver cancer, melanoma and thyroid cancer.

25. The method according to claim 20, wherein the composition is in a form suitable for administration via a route selected from the group consisting of topical, intradermal, intramuscular, intraperitoneal, intravenous, subcutaneous, intranasal, epidural, ophthalmic, and oral.

* * * * *